US011598698B1

(12) United States Patent
Laughlin

(10) Patent No.: US 11,598,698 B1
(45) Date of Patent: Mar. 7, 2023

(54) AIR TESTING COLLECTOR

(71) Applicant: Robert Laughlin, Miramar, FL (US)

(72) Inventor: Robert Laughlin, Miramar, FL (US)

( * ) Notice: Subject to any disclaimer, the term of this patent is extended or adjusted under 35 U.S.C. 154(b) by 43 days.

(21) Appl. No.: 17/469,762

(22) Filed: Sep. 8, 2021

(51) Int. Cl.
*G01N 1/24* (2006.01)
*G01N 1/22* (2006.01)
*G01N 33/00* (2006.01)
*G01N 1/02* (2006.01)

(52) U.S. Cl.
CPC .............. *G01N 1/24* (2013.01); *G01N 1/2273* (2013.01); *G01N 33/0011* (2013.01); *G01N 33/0027* (2013.01); *G01N 2001/022* (2013.01)

(58) Field of Classification Search
CPC .... G01N 1/24; G01N 1/2273; G01N 33/0011; G01N 33/0027; G01N 2001/022
USPC ........................................................ 73/31.01
See application file for complete search history.

(56) References Cited

U.S. PATENT DOCUMENTS

| | | | | |
|---|---|---|---|---|
| 2,176,462 A * | 10/1939 | McAllister | ................ | G01N 1/22 436/109 |
| 3,793,887 A * | 2/1974 | Anderson | ............. | G01N 1/2258 73/863.03 |
| 3,866,474 A * | 2/1975 | Hasselmann | ............. | G01N 1/24 73/864.34 |
| 4,226,115 A * | 10/1980 | Williams | ................. | G01W 1/08 73/864.34 |
| 4,961,916 A * | 10/1990 | Lesage | .................. | G01N 1/2205 55/318 |
| 5,693,895 A * | 12/1997 | Baxter | ................. | G01N 1/2214 73/863.22 |
| 6,139,801 A * | 10/2000 | Kawachi | ............ | G01N 33/0011 73/864.81 |
| 2001/0032519 A1* | 10/2001 | Liu | ....................... | G01N 1/2208 73/863.23 |
| 2005/0214168 A1* | 9/2005 | Lin | ....................... | G01N 1/2273 422/83 |
| 2005/0266415 A1* | 12/2005 | Ryan | ..................... | G01N 1/2208 435/6.19 |
| 2011/0197687 A1* | 8/2011 | Mihaylov | ................ | G01N 1/14 73/864.51 |
| 2011/0315011 A1* | 12/2011 | Black | .................... | G01N 1/2202 95/79 |
| 2018/0088009 A1* | 3/2018 | Later | ....................... | F16L 23/18 |
| 2022/0034761 A1* | 2/2022 | Iqbal | ...................... | B01L 3/5023 |
| 2022/0357243 A1* | 11/2022 | Lebrun-Taugourdeau | .................. | G01N 1/24 |

* cited by examiner

*Primary Examiner* — Clayton E. LaBalle
*Assistant Examiner* — Kevin C Butler
(74) *Attorney, Agent, or Firm* — Christopher J Vandam, PA; Chris VanDam

(57) ABSTRACT

A process for testing an air source by providing a bag to collect a sample of gas. Connecting the filled bag to a collector assembly that has a fraction of the interior volume of the bag. Forcing the air sample from the bag over a media dish inside the collector assembly. Removing the media for further analysis. Both the bag and the collector assembly have one way exhaust valves to prevent over-pressure and allow a limited flow through of the sample.

4 Claims, 4 Drawing Sheets

AIR TESTING COLLECTOR

CROSS-REFERENCES TO RELATED APPLICATIONS

None.

STATEMENT REGARDING FEDERAL SPONSORED RESEARCH OR DEVELOPMENT

None.

NAMES OF PARTIES TO A JOINT RESEARCH AGREEMENT

None.

REFERENCE TO A "SEQUENCE LISTING", A TABLE, OR A COMPUTER PROGRAM LISTING APPENDIX SUBMITTED ON COMPACT DISC AND INCORPORATION-BY-REFERENCE OF THE MATERIAL ON THE COMPACT DISCLOSURE

None.

STATEMENT REGARDING PRIOR DISCLOSURES BY AN INVENTOR OR JOINT INVENTOR

None.

BACKGROUND OF THE INVENTION

1. Field of the Invention

The present invention relates to air testing and analysis, and more particularly, to an improved device and method of use to safely and accurately collect air samples for quality testing.

2. Description of Related Art Including Information Disclosed Under 37 CFR 1.97 and 37 CFR 1.98

Several designs for air sampling have been designed in the past. None of them, however, include a low volume chamber with a collection medium that captures biological constituents of the tested air for laboratory analysis.

Applicant believes that the closest prior art references relate to dry media filters through which air samples are forced. The drive media filter is then removed from the filtration housing and traditional chemical analyses are performed. These prior art systems, devices and methods differ from the present invention because with a lower volume manifold, including a nutrient culture medium, smaller air samples can be tested, particularly for biological constituent components, such as, bacterium, virus, fungus, spores, pollen and other biologically derived and related airborne and suspended elements.

Other patents describing the closest subject matter provide for a number of more or less complicated features that fail to solve the problem in an efficient and economical way. None of these patents suggest the novel features of the present invention.

A brief abstract of the technical disclosure in the specification and title are provided as well for the purposes of complying with 37 CFR 1.72 and are not intended to be used for interpreting or limiting the scope of the claims.

Without limiting the scope of the invention, a brief summary of some of the claimed embodiments of the invention is set forth below. Additional details of the summarized embodiments of the invention and/or additional embodiments of the invention may be found in the detailed description of the invention below.

BRIEF SUMMARY OF THE INVENTION

It is one of the main object of the present invention to provide a device and method of use to efficiently collect an air contaminant sample in the lab or in the field.

It is another object of this invention to provide a means to collect a sample of microbial components of an air source to be analyzed.

It is another object of the present invention to provide a sampling manifold suitable for use with a low volume and low pressure ambient air sampling device.

It is yet another object of the present invention to provide a microbial air sampling device and method of collection that is effective when used by those with minimal training and experience.

It is yet another object of this invention to provide such a device and associated process that is inexpensive to manufacture and maintain while retaining its effectiveness.

Further objects of the invention will be brought out in the following part of the specification, wherein detailed description is for the purpose of fully disclosing the invention without placing limitations thereon.

These and other embodiments which characterize the invention are pointed out with particularity in the claims annexed hereto and forming a part hereof. However, for a better understanding of the invention and the advantages and objectives obtained by its use, reference can be made to the drawings which form a further part hereof and the accompanying descriptive matter, in which there are illustrated and described various embodiments of the invention.

BRIEF DESCRIPTION OF THE SEVERAL VIEWS OF THE DRAWING

With the above and other related objects in view, the invention exists in the details of construction and combination of parts as will be more fully understood from the following description, when read in conjunction with the accompanying drawings in which.

DETAILED DESCRIPTION OF THE INVENTION

Figure 1:
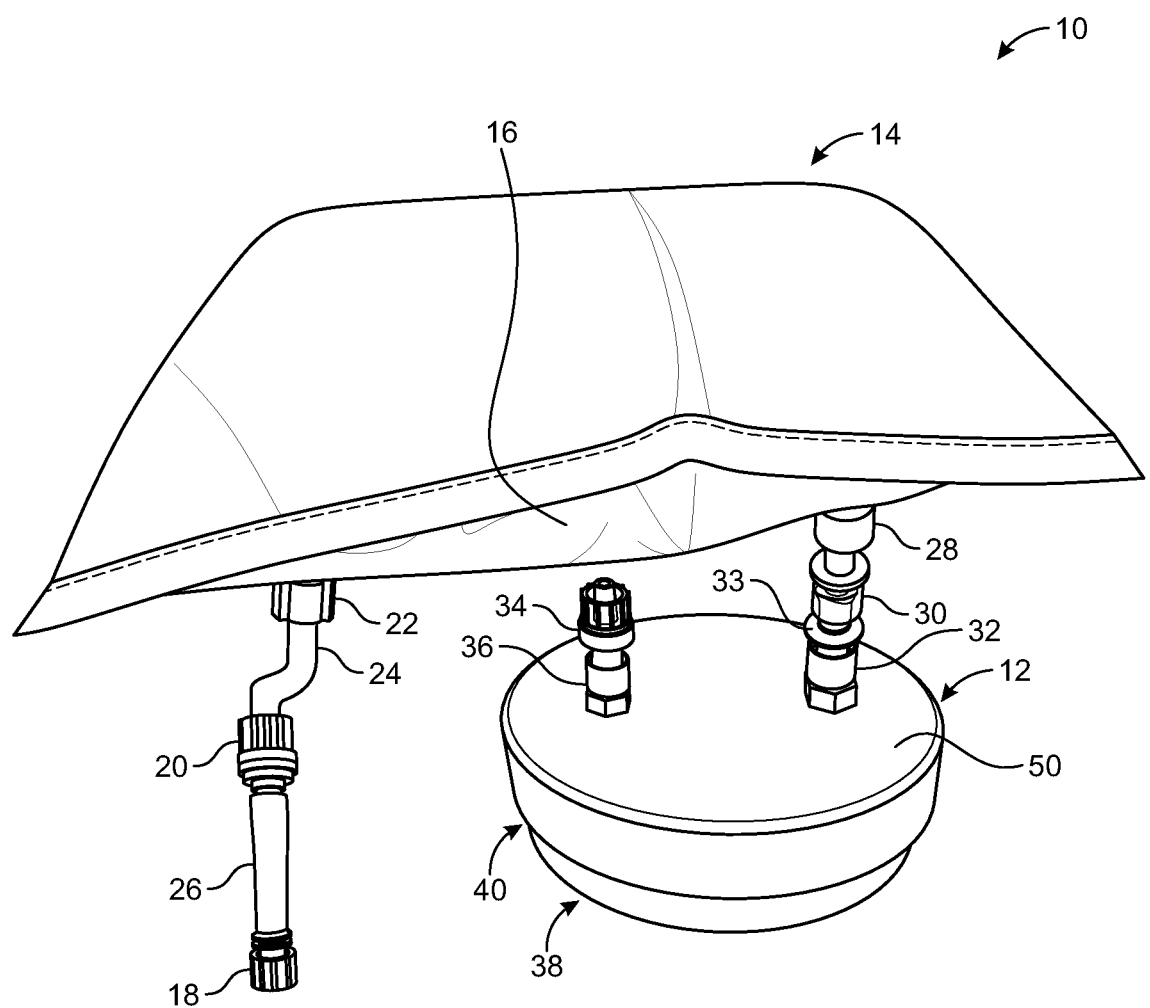
FIG. 1 shows a perspective view of an embodiment of the collector assembly attached to the sampler assembly.

While this invention may be embodied in many different forms, there are described in detail herein specific embodiments of the invention. This description is exemplary of the principles of the invention and is not intended to limit the invention to the particular embodiments illustrated and described.

For the purpose of this disclosure, like reference numerals in the figures shall refer to like features unless otherwise indicated, or is obvious by context.

The subject device and method of use is sometimes referred to as the device, the invention, the device, the collector, the air tester, the air testing process or other similar terms. These terms may be used interchangeably as context requires and from use the intent becomes apparent. The masculine can sometimes refer to the feminine and neuter and vice versa. The plural may include the singular and singular the plural as appropriate from a fair and reasonable interpretation in the situation.

Referring now to the drawings, where the present invention is generally referred to with numeral 10, it can be observed that it basically includes, among other shown and described features, a collector assembly 12, a sampler assembly 14, a bag 16, a connector 18, a valve 20, a nipple 22, an elbow 24, a tube 26, a nipple a 28, a valve 30, a nipple 32, a connector 33, a of valve 34, a nipple 36, a base assembly 38, a cover assembly 40, a side wall of 42, an aperture 44, an aperture 46, a rim 48, a top 50, a dish assembly 52, a side wall 54, a bottom 56, a rim 58, a surface 60, a side wall 62, eight surface 64, a rim 66, a bottom 68, a media 70, a pump assembly 72, a bulb 74, a coupler 76 and a valve 78.

Looking at FIG. 1, an example of the present invention is demonstrated. A sampler assembly 14 includes a bag 16. The bag 16 is a fabricated of an impermeable material, such as plastic, mylar, foil or other material within which an air samples can be received, stored and dispensed. To begin the process of analyzing a gas, a sample of that gas must first be collected.

One method of obtaining a gas sample for testing can be fairly described as connecting the connector 18 to the gas source. For some gas sources an adapter is required between the connector 18 and the gas source. For example, a scuba tank or fireman's breathing apparatus may have specific connectors and threading onto which the connector 18 is attached.

The bag 16 is initially deflated before the sample is taken. The gas source to be sampled passes through the nipple 22 and inflates the bag with a sample. The nipple 22 may also be connected to a one-way valve 20 by another fitting, such as an elbow 24. Depending on the specifics of the air source to be sampled, the tube 26 may also be positioned between the valve 20 and connector 18.

It should be appreciated that any combination of elements, such as the connector 18, tube 26, valve 20, elbow 24 and nipple 22, may be used to directly introduce an air sample into the bag. These elements are merely examples of an effective way to connect the air source to be sampled to the interior of the bag 16. Other combinations of common conduit fittings may be equally effective for connecting an air source to the bag 16 without leaking or introducing other sources of contamination to the air sampler.

The valve 20 is present in an important embodiment. The valve 20 is a one-way valve that permits the air sample to flow only toward the interior of the bag 16. The air sample in the bag 16 is then prevented from exhausting out of the bag through the nipple 22 and valve 28 combination. The nipple 22 is integral to a side panel of the bag 16 and provides a means to connect the interior of the bag 16 to the input side of the sampler assembly 14.

Each of the components of the filling side of the bag 16 fittings, for example including the connector 18, tube 26, valve 20, elbow 24 and nipple 22, should be provided to the user taking the sample in a substantially sterile condition. It is important that the air being sampled does not enter the bag 16 with any contaminants not found in the air sample itself.

On the exhaust side of the bag 16 of the sampler assembly 14 includes a nipple 28 and a valve 30. The nipple 28 and valve 30 are also provided in a sterile condition to avoid external contamination not part of the gas being sampled. The nipple 22 is integrated into a surface of the bag 16 as a means to connect the interior of the bag 16 to the exhaust side of the sampler assembly 14.

In general, the sampler assembly 14 includes a bag 16 with a predetermined interior volume. An input side includes a one-way valve 20, which does not permit air contained within the bag 16 to escape through the input side. On the exhaust side, there is a one way valve 30 that only allows the gas within the bag 16 to exhaust, and no gas may enter the bag 16 through the valve 30.

The interior volume of the bag is designed to be appropriate for the type of gas being tested. For most applications the interior volume of the bag is between about a half liter and two liters. For specialized testing, a micro-bag may have as low as ten milliliters. For other specialized testing, a macro-bag may have as much as about one hundred liters. It should be appreciated that the interior volume of the bag does not affect the character of the inventive nature of the device. It is routine for a technician to select the appropriate interior volume of the bag 16 for the particular sampling application.

Figure 2:
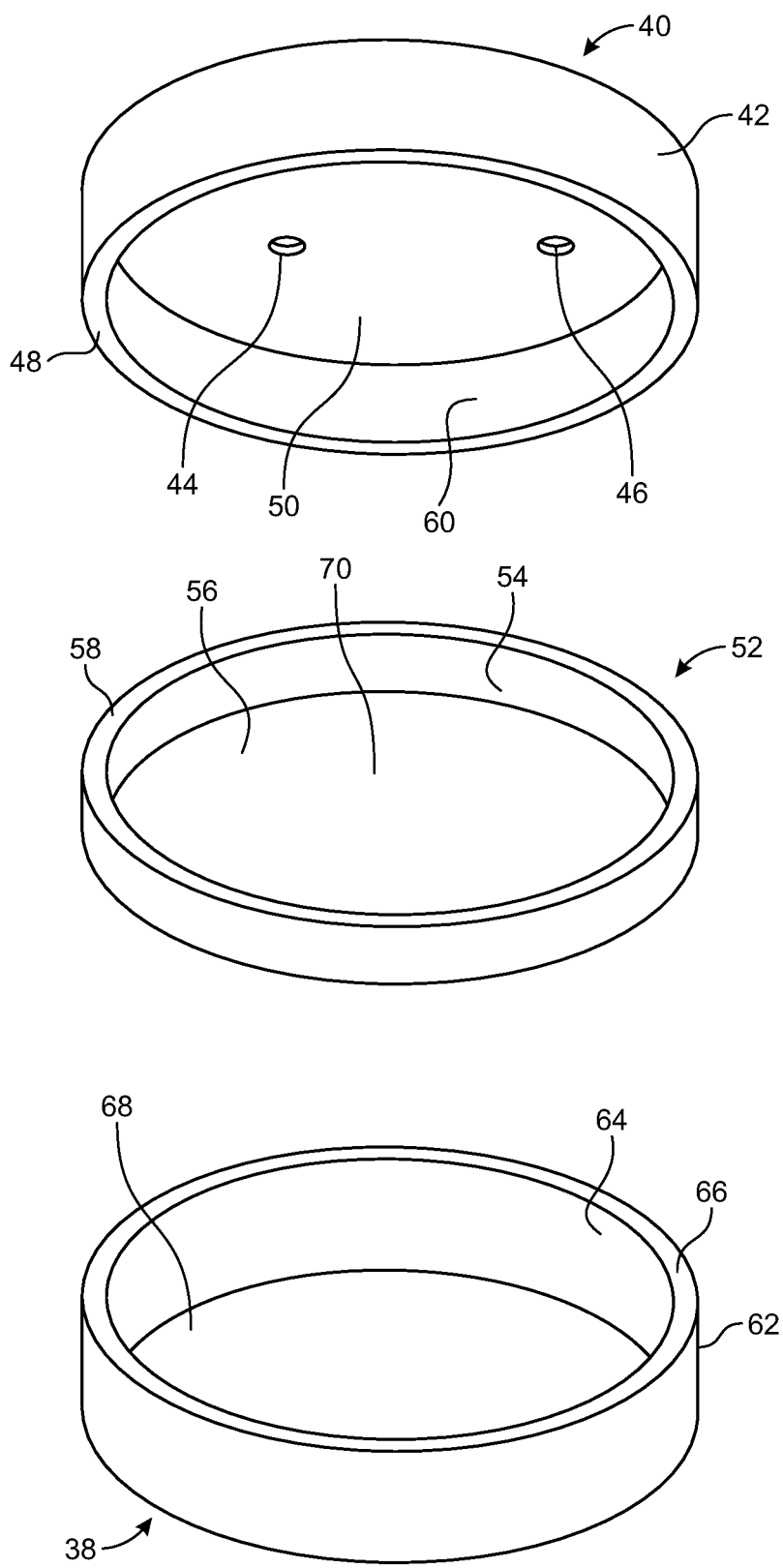
FIG. 2 shows an exploded perspective view of an embodiment of a collector assembly.
Figure 3:
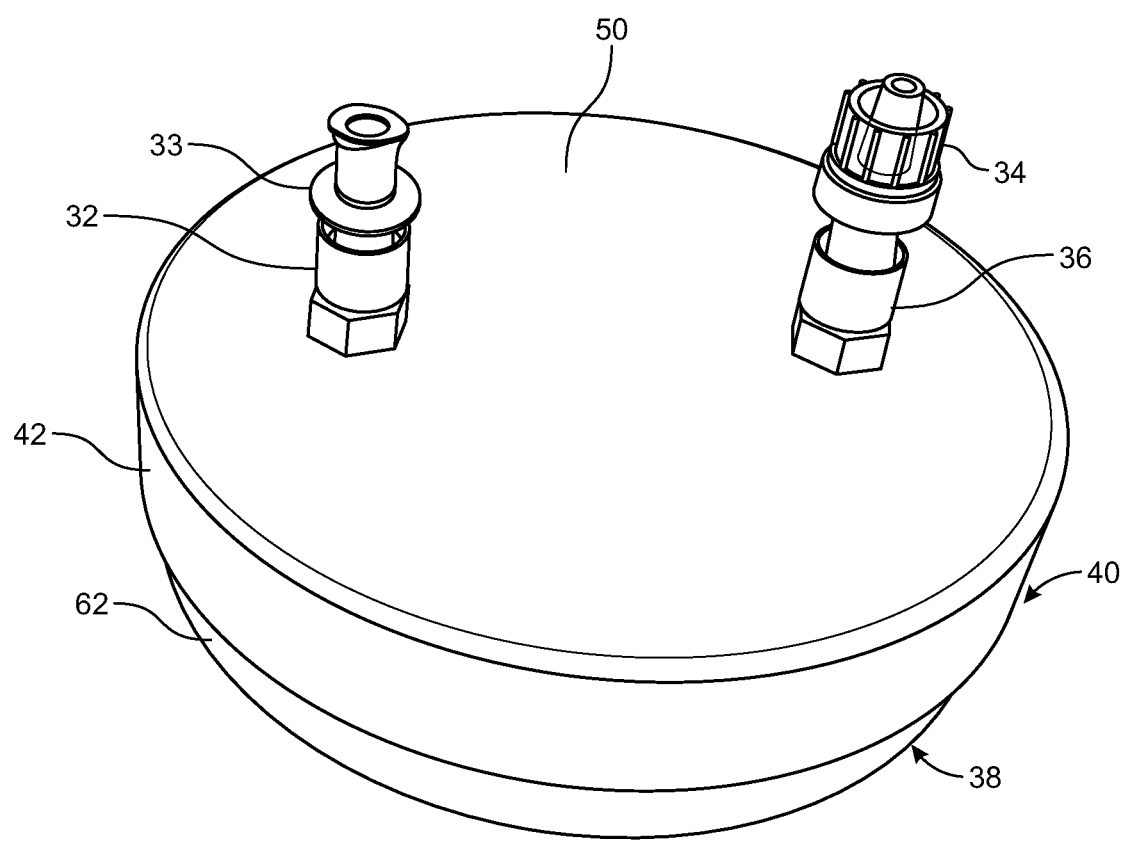
FIG. 3 shows a perspective view of a collector assembly.

Looking at FIG. 2, it can be seen that the collector assembly 12 essentially has three components: the cover assembly 40, dish assembly 52 and base assembly 38. The cover assembly 40 fits against the base assembly 38 forming a hermetic seal between the cover assembly 40 and base assembly 38. Between the cover assembly 40 and base assembly 38 is fitted the removable dish assembly 52 containing the media 70. The upper surface of the dish assembly 52 contains the media 70 and is exposed to the sample airflow entering through aperture 46 circulating over the media 70 and ultimately exhausting the device through aperture 44.

The collector assembly 12 is generally comprised of a base assembly 38 and a cover assembly 40. These cover assembly 40 in the base assembly 38 mate to form a sealed interior volume. The interior volume of the collector assembly 12 is generally between about ten percent and fifty percent of the interior volume of the collector bag 16. For most testing applications, an interior volume of the collector assembly 12 is about 30 percent of the interior volume of the bag 16 of the sampler assembly 14.

Similar to the sampler assembly 14, the collector assembly 12 includes an input aperture 46 and an exhaust aperture 44. The aperture 46 has a nipple 32 affixed to a top 50 side of the cover assembly 40. The nipple 32 is, in turn, connected to a connector 33. The connector 33 interfaces with the one-way valve 30 restricting the flow of a gas sample contained in the bag 16 to flow only from the bag 16 through the aperture 46 and to the interior of the collector assembly 12.

On a top 58 side of the cover assembly 40 is nipple 36 attached to the exhaust aperture 44. A one-way valve 34 is connected to the nipple. The one-way valve 34 permits only exhaust of sample air from the interior of the collector assembly 12. In most cases the gas vented from the valve 34 is vented to the ambient atmosphere. In other cases, depending on the nature of the gas being collected and sampled, the exhaust gas emitting from the valve 34 may be captured and collected.

A dish assembly 52 is placed onto a bottom 68 of the base assembly 38. The diameter of the dish assembly 52 is dimensioned to fit within the side wall 62 of the base assembly 38. The height of the side wall 54 of the dish assembly 52 is dimensioned so that the dish assembly 52 fits entirely within the collector assembly 12 when they cover assembly 40 is fit over the base assembly 38.

The dish assembly 52 contains a media 70 component on a bottom 56 surface. The media 70 may be comprised of agar, gelatin, bio-retaining material, culture media, oil, oil emulsion, adhesive material or other material adapted to capture and bind to particulate matter introduced to the collector assembly 12 through the input aperture 46. An important aspect of the immediate 70 is that a sample of microscopic constituents of the sample air is passed from the input aperture 46 to the interior of the dish assembly 52 where a sample is adhered to the media 70 before the carrier sampled air is exhausted through aperture 44.

The media 70 should be provided in a sterile condition prior to an air sample in the bag being passed over the media 70 inside the collector assembly 12. By analyzing the media 70 after a volume of air from the bag 16 has cycled through the interior of the collector assembly 12, the quality, quantity and nature of the constituent particulate or biological matter can be ascertained.

In one version of the collector assembly 12 design, the height of the side wall 54 is less than the height of the side wall 62 so that the rim 58 of the dish assembly 52 is below the rim 66 of the base assembly 38. In this way the dish assembly 52 fits within the side wall 62 and entirely below the rim 66 and does not interfere with the seal between the cover assembly 40 and the base assembly 38.

The side wall 54 of the district assembly 52 is also dimensioned to fit snugly inside the rim 66 of the base assembly 38 to avoid substantial air space between the dish assembly 52 and the base assembly 38. By having the dish assembly 52 fit inside the base assembly 38, nearly the entirety of the sample gas entering the interior of the collector assembly 12 through the aperture 46 will be circulated inside the dish assembly 52 and over the media 70 before being exhausted through aperture 44.

Other analogous variations of the collector assembly 12 may be characterized in that the rim 58 of the dish assembly 52 is sealed tight against the top 50 surface of the cover assembly 42 to create a seal so that gas entering aperture 46 only circulates inside the dish assembly 52 before exhausting through aperture 44. In this embodiment, the base assembly 38 is adapted to hold the dish assembly 52 height against the interior top 50 of the cover assembly 40.

The base assembly 38 may be threaded onto the cover assembly 40, thereby sandwiching the dish assembly 52 between the cover assembly 40 and base assembly 38. Alternatively, the cover assembly 40 may be friction fit against the base assembly to ensure that the cover assembly 40 dish assembly 52 and base assembly 38 stay sealed together during the sampling procedure. Other means of connecting the cover assembly 42 the base assembly 38 may be equally effective. These may include, for example, a magnetic attachment, an adhesive attachment, a tape encircling the side wall 42 and side wall 62 joining the rim 48 with the rim 66 to ensure a hermetic seal between the cover assembly 40 and base assembly 38.

A typical use of the air testing collector will initially include providing a sampler assembly 14 with a completely evacuated bag 16 to the technician for collecting the sample of gas to be tested. The sampler assembly 14 is used by the technician in the field to collect a sample. The sampler assembly 14 is sealed and sent to the testing lab where the sampler assembly 14 is connected for the first time to the collector assembly 12.

The collector assembly 12 is generally not provided with the sampler assembly 14. The collector assembly 12 is utilized in the testing lab. The sampler assembly 14 is simplified to be used by a technician with minimal training. The technician need only fill the bag 16 with the gas sample to be tested. The sampler assembly 14 is generally a single use device. Whereas, the collector assembly 12 can be sanitized, a new dish assembly 52 is fitted and then be reused for testing another gas sample in the sampler assembly 14.

The technician first affixes the connector 18 to the source of gas to be sampled. The gas is then selectively initiated, for example by opening a valve of a tank. The gas sample then begins to flow through the connector 18 and tube 26 through the one-way valve 20, through the elbow 24, through the nipple 22 and ultimately into the bag 16.

The bag 16 is then inflated with the gas sample to be tested. In some versions of the testing procedure, access air is delivered into the bag 16 through the connector 18 which causes an over-pressure in the bag 16 and access pressure is vented through nipple 28 in the valve 30. Essentially, the sample of the gas being tested is greater than the bag 16 can contain. A portion of the air being collected completely passes through the bag 16 before the valve 32 connects to the collector assembly 12.

Often, during practice, the sampler assembly 14 is filled with the air sample to be tested on a location remote from the lab testing facility. The sampler assembly 14 is shipped to the testing lab. During shipping the environmental factors experienced by the bag 16 may vary. For example, if delivered by air the ambient air pressure may be significantly affected and cause the bag 16 to increase or decrease pressure. Similarly, temperature differences through other modes of transport may also affect the pressure inside the bag.

To remedy overpressure situations in the bag 16, the one-way valve is preselected to allow automatic venting if pressure exceeds a pre-set value. For example, the valve 30 may open and vent if a pressure is experienced greater than approximately two to five psi. The pressure at which the valve 30 may vent is determined by the volume of the bag 16 and the structure and materials that the bag 16 are made. When determining the appropriate release pressure of the valve 30, the bag and gas should be considered. In some applications, the pressure could be as low as a about a half psi to twenty psi. The vent pressure release should be a high enough to prevent the sample from excessive leakage out of the bag 16 during normal acquisition of the sample and transport.

The valve 20 also is selected with a predetermined pressure at which it opens under supply pressure to allow gas to pass through the nipple 22 and fill the bag 16. Generally, this pressure is very low to not restrict the ability for gas to enter the bag 16 through the valve 20. In most applications, the one-way valve 20 will have from about zero resistance to about one psi. The degree of resistance of the one-way valve 20 may be selected by considering the nature and source of the supply gas to be sampled and the construction of the bag 16.

Figure 4:
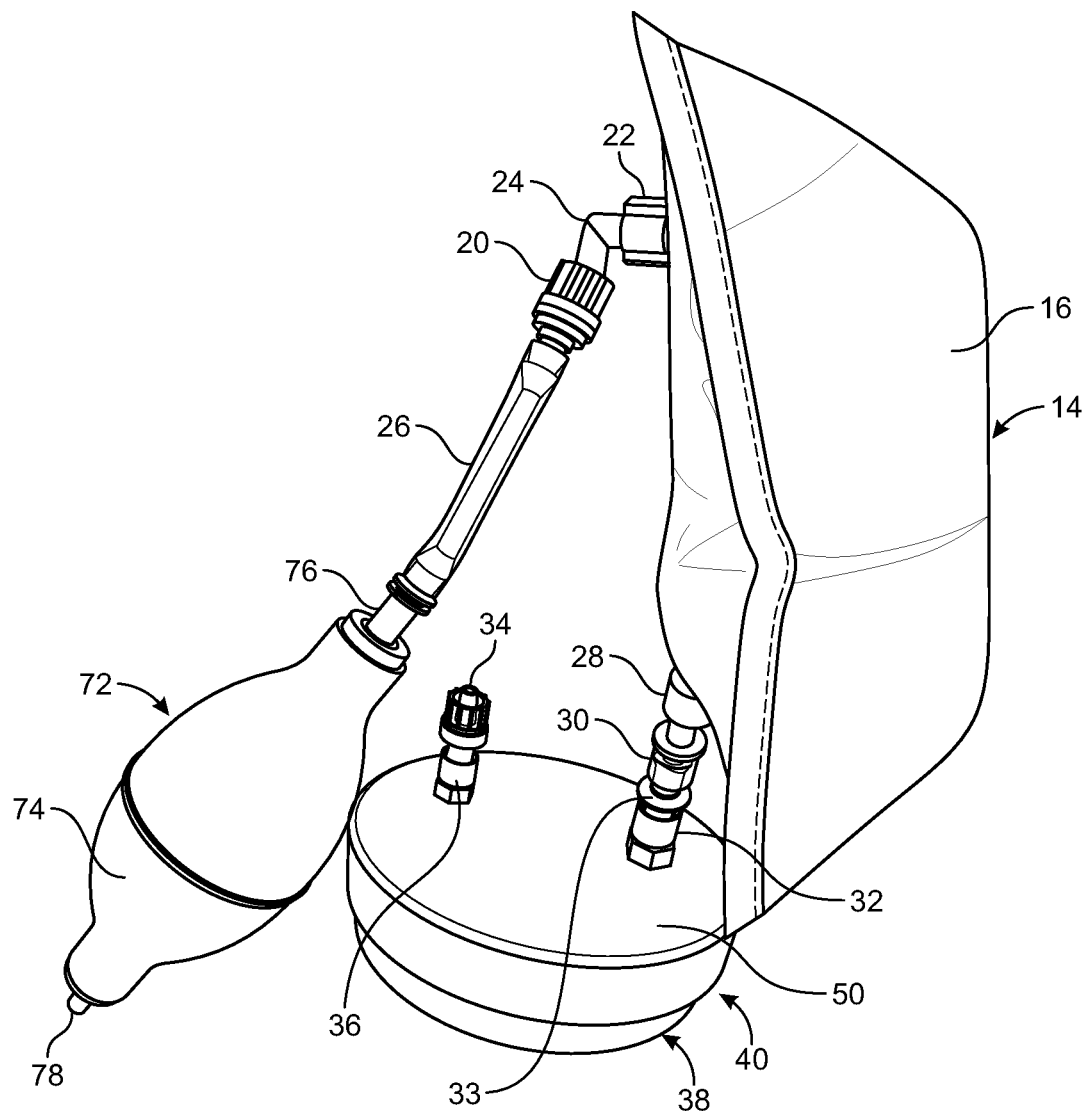
FIG. 4 shows a perspective view of a sampler assembly connected to a collector assembly.

FIG. 4 demonstrates both a pump assembly 72 that introduces ambient air to the sampler assembly 14 as well as the connection between the sampler assembly 14 and connector 33 on the top 50 surface of the cover assembly 40. It should be appreciated that the pump assembly 72 is generally not connected to the collector assembly 12 during any normal mode of operation.

For a typical use of the pump assembly 72, as shown in FIG. 4, the sampler assembly 14 and pump assembly 72 are connected at the coupler 76. In other versions of the sampler assembly 14, as shown and described above, the pump assembly 72 and coupler 76 are substituted with a pressurized gas source.

The bulb 74 of the pump assembly 72 is generally hollow and flexible. A hand of the user may compress the bulb 74 thereby forcing air contained in the bulb 74 through the coupler 76, tube 26, valve 20, an elbow 24 and nipple 22 delivering that air sample into the bag 16. As the user's hand relaxes from the bulb 74, the bulb 74 returns to its normal on compress state by drawing in a sample of ambient air through one-way valve 78.

The bulb 74 is repeatedly compressed to pump air into the bag 16 and then draws in fresh air through one-way valve 78 into the bulb 74 when pressure is released from the bulb 74. By repeatedly pumping the bulb 74, the pump assembly 72 can be used to fully inflate the bag 16 of the sampler assembly 14.

Before the pump assembly 72 is connected to the sampler assembly 14 at the coupler 76, the bulb 74 may be squeezed several times to expel the sterile air in a newly unpackaged pump assembly 72. Several pumps of the bulb 74 will cycle ambient air through the interior of the bulb to ensure that only ambient air is delivered into the bag 16 and not the sterilized air of an unused pump assembly 72.

By using the manual pump assembly 72 any user can deliver a sample of ambient air in a room through the valve 78 of the pump assembly 72 into the sampler assembly. After unsealing the pump assembly 72 from its sterile packaging, a few pumps on the bulb 74 clears out the sterile error delivered inside the ball the 74 and replaces it with ambient air from the room. The user then connects the pump assembly 72 to the sampler assembly 14 and compress of the bulb several more times to manually pump air from the open air into the bag 16.

The one-way valve 78 only allows ambient air to enter the bulb 74. One-way valve 20 is oriented in the same direction of flow as one-way valve 78, both only allowing airflow toward the bag 16. The bag 16 may be supplied with sufficient air by the pump assembly 72 to allow some venting of overpressure gas through the valve 30 back into the ambient air. Note that the sampler assembly 14 is not connected to the collector assembly 12 when the ambient air samples being gathered.

Once the bag 16 is filled with the gas sample to be tested, the sampler assembly 14 is sent to a testing facility laboratory. The sampler assembly 14 may be shipped in a container or hand delivered to the testing facility. Because the bag 16 is gas-impervious, the sample can remain in the bag 16 for the anticipated duration of transporting to the lab. Because of the one-way valve 20 and 30, no additional air is possible to enter the bag during transport.

When the gas to be tested is delivered to the laboratory in the bag 16, it is affixed to the collector assembly 12, similar to that shown in FIG. 1. With a sterile dish assembly 52 and media 70 therein, the contents of the bag 16 is prepared for dispensing through the nipple 32 and into the interior of the collector assembly 12.

To begin the flow of sample gas from the interior of the bag 16 into the collector assembly 12, the bag 16 may be manually squeezed by the hands of the technician taking the sample to pressurize as the bag 16 and forcing the air sample to exhaust the bag 16 through nipple 28, one-way valve 30, connector 33 and nipple 32 into the interior of the collector assembly 12.

An alternative method of forcing the air into the collector assembly 12 may be done by connecting a vacuum source to one-way valve 34 to mechanically pull the air sample from the bag 16 into the interior of the collector assembly 12. Generally, care should be taken to avoid completely emptying the bag 16 of gas to prevent ambient air from being drawn in through nipple 22 into the interior of the bag 16 during the sample collection testing process. A timer, flowmeter or other similar device may be used to ensure that a sufficient gas sample from the bag 16 is passed through the collector assembly 12 for a quality sample and also without fully exhausting the bag 16.

As noted above, because the volume of the bag 16 is generally greater than the interior volume of the collector assembly 12, the sample air flows through the interior of the collector assembly 12 to completely replace the sterilized air therein. Excess gas is exhausted through nipple 36 and one-way valve 34 and either collected or exhausted into the atmosphere.

Once the sampler assembly 14 has collected and delivered the gas to be collected into the collector assembly 12, the sampler assembly 14 is discarded. This helps ensure that a bag is not reused. A reused bag could introduce contaminants from a prior testing into a subsequent test and should be avoided. The materials from which the sampler assembly 14 are constructed are such that it is cheaper, easier and more sanitary to replace the sampler assembly than to try to clean it for a subsequent test.

In contrast, the collector assembly 12 may be reused many times. The dish assembly 52 and sterile media 70 used inside the collector assembly 12 may be replaced for each test. To prepare the collector assembly 12 for a subsequent test, the cover assembly 40 and base assembly 38 are sterilized and a new dish assembly 52 is inserted. The collector assembly 12 generally remains in the testing laboratory.

After the air sample has been expelled from the sampler assembly 14 through the collector assembly 12, the sampler assembly 14 is disconnected from the collector assembly 12 and the collector assembly 12 is brought to a sterile station where the cover assembly 40 is separated from the base assembly 38. The dish assembly 52 containing the media 70 that has at that point been exposed to the pathogens and particulates suspended in the gas sample in the bag 16. The dish assembly 52 is then presented for microscopic, chemical and/or biologic testing to ascertain the nature, quantity and quality of the collected material on the media 70.

The media 70 in the dish assembly 52 may be any type of material that will allow a contaminant in an air sample passing through the collector assembly 12 to become trapped for later analysis. For example, a common agar on a petri dish provides a low cost and suitable surface that is both sterile and readily adheres to airborne contaminants. Other gelatinous materials commercially available may be suitable as well. The chemical analysis procedure as well as the nature of the gas source being tested may be considered for compatibility with a particular media 70.

Certain viscous oils and lipids may also be suitable coatings for the bottom 56 of the dish assembly 52. Oils and oil emulsions fabricated from purified material can provide a suitable surface onto which contaminant particles are collected and can effectively be isolated to avoid skewing test results. Similarly, adhesive gels or adhesive film layers on the bottom 56 of the dish assembly 52 may effectively trap solids or gases in the air sample being tested. It should be appreciated that the terms air sample, gas sample, testing sample or any other analogous terms refer to the gaseous body that the user intends to test for compliance with industry standards.

An important version of the process for testing the gas sample may be fairly characterized as first providing a sampler assembly and a collector assembly. The sampler assembly is comprised of a bag to hold the gas sample configured with a panel on each side with a seal around the periphery creating a first interior. The first interior is configured with a first predetermined volume. The predetermined volume is selected based on the nature of the gas sample and anticipated contaminants. The side panel has a first aperture including a one-way valve that is configured input a gas sample into the interior of the bag. A second aperture is provided in the side panel which includes a one-way valve configured to exhaust the gas from the interior of the bag. This second one-way valve is configured to permit an exhaust flow only above a predetermined first pressure. This pressure is selected by the size of the bag, the nature of the gas being tested and the pressure is that the bag may be subjected to. Generally, this will be in a range from about 0.5 psi and ten psi, but may be above or below that range if particular requirements are needed as are obvious from the application situation. Next, a gas source to be tested, including a gas, is selected and identified. The user then connects the gas source to the interior of the bag through the first one-way valve. Sometimes an adapter fitting or longer tubing or different standard fittings are required. Then, delivering a portion of the gas from the gas source to the first interior of the bag. This is the primary sample to be tested. If needed, then venting the gas from the first interior of the bag through the second one-way valve when the interior of the bag exceeds the first pressure. This is a blow through feature that automatically limits the amount of gas inside the bag and prevents over-pressure in the bag. The collector assembly is comprised of a cover assembly, a base assembly and a dish assembly. The cover assembly and base assembly are configured to join together at an airtight seal with the dish assembly disposed therein with the open top of the dish assembly facing the underside of the lid assembly. The collector assembly is configured to have a second interior between the cover assembly and the bottom surface of the dish assembly. The second interior is configured with a second predetermined volume. The second volume is less than thirty percent of the first volume. The dish assembly has a bottom surface covered in a media. Affixed to a third aperture in the cover assembly is a nipple. Affixed to a fourth aperture in the cover assembly is a third one-way valve configured to exhaust the gas sample from the second interior of the collector assembly. The third one-way valve is configured to permit an exhaust flow only above a predetermined first pressure, generally between about 0.1 psi and 10 psi. These psi values could vary depending on the nature of the gas being tested, the bag and the volume of the collector assembly. Then, connect the second one-way valve to the nipple so that the interior of the bag containing the gas sample is in communication with the interior of the collector assembly. Then, expelling the gas in the first interior through the second one way valve and the nipple into to the second interior thereby exposing the media to the gas and is constituent parts. Venting a portion of the gas from the second interior through the third one-way valve when the second interior exceeds the second pressure. Removing the dish assembly from inside the collector assembly providing the media in the dish assembly for analysis. Optionally, the gas source is a pump assembly that draws in ambient air and pumps ambient air into the bag, for example, the hand pump in FIG. 4. This could also be another type of manual or electrically powered pump. Optionally, the gas source is a pressurized gas cylinder that is ducted to vent a gas from the pressurized cylinder into the bag. Fittings, adapters and tubing may be used. Optionally, the media is selected from one of: an agar, a gelatin, an oil, an oil emulsion, an adhesive gel or an adhesive film layer. Any material that 'sticks' to airborne particles in the sample and that is compatible with testing procedures may be effectively used.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

I claim:

1. A process for testing a gas sample comprised of:

providing a sampler assembly and a collector assembly;

the sampler assembly is comprised of a bag configured with a side panel and a first interior;

the first interior is configured with a first predetermined volume;

affixed to a first aperture in the side panel is a first one-way valve configured to input a gas sample to the first interior;

affixed to a second aperture in the side panel is a second one-way valve configured to exhaust the gas sample from the first interior;

the second one-way valve is configured to permit an exhaust flow only above a predetermined first pressure;

selecting a gas source comprised of a gas;

connecting the gas source to the interior of the bag through the first one-way valve;

delivering a portion of the gas from the gas source to the first interior of the bag;

venting the gas from the first interior of the bag through the second one-way valve when the interior of the bag exceeds the first pressure;

the collector assembly is comprised of a cover assembly, a base assembly and a dish assembly;

the cover assembly and base assembly are configured to join together at an airtight seal with the dish assembly disposed therein;

the collector assembly is configured to have a second interior between the cover assembly and the bottom surface of the dish assembly;

the second interior is configured with a second predetermined volume;

the second volume is less than thirty percent of the first volume;

the dish assembly has a bottom surface covered in a media;

affixed to a third aperture in the cover assembly is a nipple;

affixed to a fourth aperture in the cover assembly is a third one-way valve configured to exhaust the gas sample from the second interior of the collector assembly;

the third one-way valve is configured to permit an exhaust flow only above a predetermined first pressure;

connecting the second one-way valve to the nipple;

expelling the gas in the first interior through the second one way valve and the nipple into to the second interior thereby exposing the media to the gas;

venting the gas from the second interior through the third one-way valve when the second interior exceeds the second pressure;
removing the dish assembly from inside the collector assembly;
providing the media in the dish assembly for analysis.

2. The process of claim 1 further characterized in that the gas source is a pump assembly (72) that draws in ambient air and pumps ambient air into the bag.

3. The process of claim 1 further characterized in that the gas source is a pressurized gas cylinder that is ducted to vent a gas from the pressurized cylinder into the bag.

4. The process of claim 1 further characterized in that the media is selected from one of: an agar, a gelatin, an oil, an oil emulsion, an adhesive gel or an adhesive film layer.

* * * * *